(12) United States Patent
Freedman et al.

(10) Patent No.: US 6,780,194 B2
(45) Date of Patent: Aug. 24, 2004

(54) CIRCUMCISION CLAMP

(76) Inventors: Donald S. Freedman, 4063 Salisbury Rd., Suite 202, Jacksonville, FL (US) 32216; David F. Campbell, 1835 US 1 South, #115, St. Augustine, FL (US) 32086

( * ) Notice: Subject to any disclaimer, the term of this patent is extended or adjusted under 35 U.S.C. 154(b) by 61 days.

(21) Appl. No.: 10/178,803

(22) Filed: Jun. 24, 2002

(65) Prior Publication Data

US 2003/0236532 A1 Dec. 25, 2003

(51) Int. Cl.[7] .............................................. A61B 17/42
(52) U.S. Cl. ..................................... 606/118; 606/120
(58) Field of Search ....................... 606/118, 119, 606/120, 151, 157, 142

(56) References Cited

U.S. PATENT DOCUMENTS

| | | |
|---|---|---|
| 1,918,700 A | 7/1933 | Harris |
| 2,548,670 A | 4/1951 | Hyatt |
| 2,686,521 A | 8/1954 | Sheldon et al. |
| 2,747,576 A | 5/1956 | Bronstein |
| 3,277,895 A | 10/1966 | Johnson |
| 3,323,208 A | 6/1967 | Hurley, Jr. |
| 3,566,873 A | 3/1971 | Melges |
| 3,669,115 A | 6/1972 | Melges |
| 3,678,935 A | 7/1972 | Bronstein |
| 3,706,312 A | 12/1972 | Melges |
| 3,741,215 A | 6/1973 | Ayad |
| 3,757,787 A | 9/1973 | Gottlieb |
| 4,212,303 A * | 7/1980 | Nolan .................... 606/120 |
| D287,763 S | 1/1987 | Porat et al. |
| 4,938,215 A * | 7/1990 | Schulman et al. ........ 606/120 |
| 5,649,933 A | 7/1997 | Singh |
| 5,797,921 A | 8/1998 | Cimini et al. |
| 5,947,980 A * | 9/1999 | Jensen et al. ............ 606/120 |

* cited by examiner

Primary Examiner—Kevin T. Truong
(74) Attorney, Agent, or Firm—Arthur G. Yeager

(57) ABSTRACT

The clamp includes a passage adjacent to a pivot connection and into which a corresponding pivot pin is at least partially displaced from its original position into a position in which the circumcision clamp becomes inoperative. In one embodiment, the passage is located at one end of the latching member having a notch that is adjacent to a spur so that, when the clamp is moved to a closed position, the spur slips into the notch. The spur and notch resist movement of the latching member thereby causing the pivot pin to be forcibly displaced from its original position into an inoperative position. Select elements of the clamp may be formed of transparent plastic material for allowing a circumcision operator to monitor the glans penis therebeneath so that same is not damaged during a circumcision. Alternately, the clamp may be formed of aluminum and stainless steel. In such an embodiment, the passage is located at one end of the handle. As the handle moves to an open position from a closed position, the corresponding pivot pin at the end of the handle is forcibly displaced at least partially into the passage and thereby rendering the clamp inoperative. Such an embodiment of the clamp may be sent back to the manufacturer to be refurbished and resterilized for reuse.

19 Claims, 4 Drawing Sheets

CIRCUMCISION CLAMP

CROSS REFERENCE TO RELATED APPLICATIONS

Not Applicable.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Technical Field

This invention relates to a circumcision clamp and, more particularly, to a circumcision clamp having a pivot pin that becomes offset after performing a circumcision procedure and thereby rendering the clamp inoperative to perform another circumcision.

2. Prior Art

Circumcision instruments are well known in the art. Such instruments are commonly used to remove prepuce from a penis for medical and/or religious reasons, for example. Some conventional circumcision instruments may be discarded after performing a circumcision procedure for ensuring that sterile and dependable circumcision instruments will be employed in subsequent procedures. As a result, hospitals and medical doctors are burdened with the higher costs associated with the manufacture and employment of a new circumcision instrument for each patient. Unfortunately, the costs of this shortcoming are ultimately passed on to the patients.

A particularly popular circumcision clamp widely employed is disclosed in U.S. Design Pat. No. 287,763 to Porat et al. Such a circumcision clamp is known in the industry to be both reliable and safe. Porat et al.'s clamp is made from stainless steel and is reusable after sterilization. Unfortunately, some shortcomings of such a circumcision clamp are its relatively high cost and heavy weight as well as wear on the cam lever which effects the proper functioning of the clamp during use.

Other circumcision clamps employed in the industry are disclosed in U.S. Pat. Nos. 3,566,873, 3,706,312 and 3,669,115 to Melges. Such clamps may be relatively lightweight because they can be made from plastic materials. In addition, such clamps include a hook latch member that breaks off after each use thereby making the clamp inoperable and disposable. Unfortunately, a shortcoming of such prior art circumcision clamps is their inability to be refurbished for reuse.

Yet other circumcision instruments are disclosed in U.S. Pat. Nos. 5,649,933 and 5,797,921 to Singh and Cimini et al., respectively. Such clamps also may be made from plastic materials. Accordingly, such clamps weigh less than conventional stainless steel clamps. Unfortunately, similar to other prior art clamps, a shortcoming of these clamps is their inability to be refurbished for reuse.

BRIEF SUMMARY OF THE INVENTION

In view of the foregoing background, it is therefore an object of the present invention to provide a lightweight and dependable circumcision clamp having low manufacturing costs. Another object of the present invention is to provide a circumcision clamp that can be refurbished and resterilized for reuse. These and other objects, features, and advantages of the present invention, are provided by a circumcision clamp for performing a circumcision operation and including an engaging section for receiving prepuce to be removed during a circumcision procedure, securing means for tightly maintaining the engaging section in a closed position and for releasing the engaging section to be opened. The securing means includes a latching member and a handle movably connected thereto. The clamp also has a pair of pivot connections for respectively connecting a first end of the latching member to the engaging section and a second end of the latching member to the handle. Each of the pivot connections includes a pivot pin. A passage is adjacent to one of the pivot connections into which a corresponding one of the pivot pins is at least partially displaceable when force is exerted against the one pivot pin in a direction generally toward the passage for causing the one pivot pin to be displaced from its original position into a position in which the circumcision clamp becomes inoperative.

The engaging section includes an elongate first member and an elongate second member and a main pivot connection adjacent a first end of each member for movably connecting the first and second members. The first and second members may be formed of transparent plastic material for allowing a circumcision operator to monitor the glans penis therebeneath so that same is not damaged during a circumcision.

The first end of the latching member includes a spur for resisting movement of the securing means from a closed position to an open position. The first member includes a notch generally at a second end thereof and adjacent to the spur so that, when the securing means is moved to a closed position, the spur slips into the notch. The spur and notch resist movement of the securing means and cause the one pivot pin to be forcibly displaced from its original position into the inoperative position.

The notch is generally midway between upper and lower surfaces of the second end of the first member and has a generally smooth shoulder for guiding the spur therein when the latching member is moved to a closed position. The one pivot connection is formed of deformable material so that the one pivot pin at least partially enters the passage when the latching member is moved to an open position after a circumcision.

The passage has a width narrower than the diameter of the one pivot pin so that same can only partially enter the passage when sufficient pressure is applied to the one pivot pin in a general direction of the passage. The passage is juxtaposed to the one pivot connection and both are located at the second end of the first member. The passage extends from the one pivot connection towards an outer edge of the first member. The second end of the first member is bifurcated and has an upper portion and a lower portion for receiving the first end of the latching member therebetween. The passage is located in at least one of the bifurcated upper and lower portions of the first member. The latching member and pins are formed of steel and remaining elements of the clamp are formed of plastic material. Advantageously, the present invention will be lighter, yet just as strong as prior art circumcision instruments made from stainless steel, for example, as well as more affordable for the patient.

In an alternate embodiment, a circumcision clamp includes an engaging section for receiving prepuce to be removed during a circumcision procedure, securing means for tightly maintaining the engaging section in a closed position and for releasing the engaging section to be opened. The securing means includes a latching member and an elongated handle movably connected thereto. A pair of pivot connections respectively connects a first end of the latching member to the engaging section and a second end of the latching member to one end of the handle. Each of the pivot connections includes a pivot pin. The one end of the handle includes a passage into which one of the pivot pins is at least partially displaceable when force is exerted against the one pivot pin in a direction generally toward the passage to cause the one pivot pin to be displaced from its original position into a position in which the circumcision clamp becomes inoperative.

The one end of the handle is bifurcated and has an upper portion and a lower portion for receiving the latching member therebetween. The passage is located in at least one of the upper and lower portions of the bifurcated end and is adjacent to one of the pivot connections. The passage at least partially receives the one pivot pin from the original position when the securing means is moved to an open position after a circumcision. The passage has a width narrower than the diameter of the one pivot pin so that the one pivot pin can only partially enter the passage when sufficient pressure is applied to the one pivot pin in a general direction of the passage.

The engaging section includes an elongate first member and an elongate second member and a main pivot connection adjacent a first end of each member for movably connecting the first and second members. The one pivot connection is formed of deformable material so that the one pivot pin at least partially enters the passage when the securing means is moved to an open position after a circumcision. Further, the latching member and pins are formed of steel and the remaining elements of the clamp are formed of aluminum. Advantageously, the inoperable clamp may be returned to the manufacturer for refurbishing the handle and/or the one pivot pin and for resterilizing the circumcision clamp for resale and/or reuse.

BRIEF DESCRIPTION OF THE SEVERAL VIEWS OF THE DRAWING

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

DETAILED DESCRIPTION OF THE INVENTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this application will be thorough and complete, and will fully convey the true scope of the invention to those skilled in the art. Like numbers refer to like elements throughout, and prime and double prime notations are used to indicate similar elements in the two embodiments set forth herein.

Figure 1:
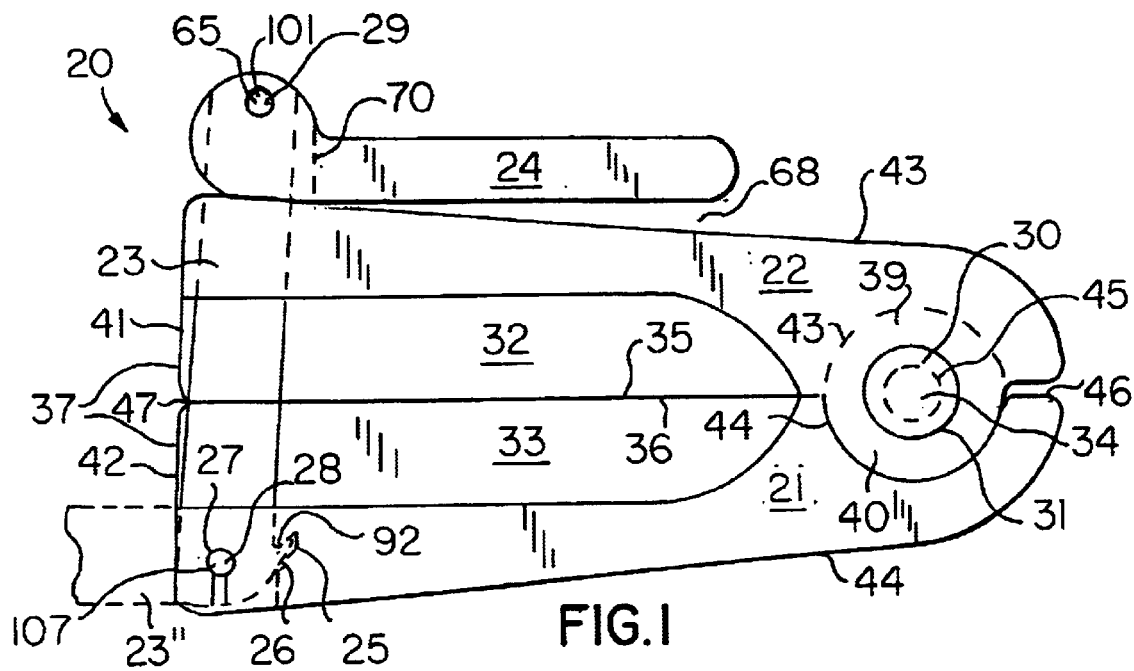
FIG. 1 is a top plan view of a circumcision clamp in accordance with the first embodiment of the present invention.
Figure 2:
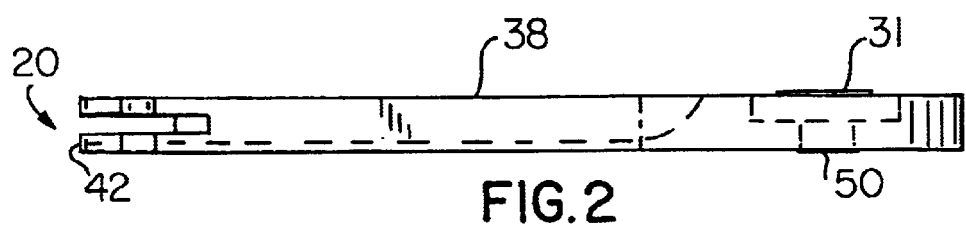
FIG. 2 is a front elevational view of the circumcision clamp shown in FIG. 1, excluding the latching member.

Referring initially to FIGS. 1 and 2, a circumcision clamp 20 for performing a circumcision operation is shown. Clamp 20 includes an upper or first elongate member 21 and a lower or second elongate member 22, latching member 23, handle 24, and a plurality of pivot connections 107, 101, 34 secured by a plurality of pivot pins 28–30, respectively. First and second elongate members 21, 22 define the engaging section of clamp 20. Latching member 23 and handle 24 define the securing means for tightly maintaining the engaging section in a closed position during use.

All parts of clamp 20, except latching member 23 and plurality of pivot pins 28–30, are preferably made from tough rigid plastic materials. Such plastic materials may include nylon, polypropylene and polycarbonates, for example. Advantageously, clamp 20 may be manufactured by injection molding processes known in the industry, for example, and thereby reduce manufacturing costs. Latching member 23 and plurality of pivot pins 28–30 are preferably made from durable and non-corrosive materials such as stainless steel and titanium, for example. It is noted that conventional circumcision procedures to be performed with the present invention are known in the art and will not be discussed herein.

First and second members 21, 22 are connected at main pivot connection 34 at a first end of each member. Accordingly, such members cooperate with each other for opening and closing the engaging section. A portion of respective second ends of first and second members 21, 22 is curved so that v-shaped aperture 47 is formed when faces 35, 36 engage. When clamp 20 is in a closed position, engaging faces 35, 36 abut each other along a horizontal axis thereof. The spatial relationship of such faces increases as clamp 20 is moved to an open position. When first and second members 21, 22 are pivoted apart from each other, the distance between opposing faces 35, 36 is greatest at ends 41, 42 and linearly decreases along faces 35, 36 towards main pivot connection 34.

For performing a circumcision procedure, the engaging section must be in a fully closed position with a prepuce (not shown) engaged therebetween. Accordingly, the portion of the prepuce extending above faces 35, 36 preferably is removed from a penis (not shown). Bowed sections 32, 33 extend generally along the length of first and second members 21, 22 and form a symmetric cavity 37 when at a closed position. The cavity has a substantially conical shape similar to the shape of clamp 20 and extends from top surface 38 downward in a sloped angle towards each other and terminating at engaging faces 35, 36. Cavity 37 extends from ends 41, 42 of corresponding first and second 21, 22 members along the length of clamp 20 and stops before arcuate portions 39, 40.

The width of cavity 37 is most thin at engaging faces 35, 36 and gradually tapers upward and away therefrom to about midway of first and second members 21, 22, respectively. Accordingly, cavity 37 provides a concave surface for accessing a prepuce engaged between opposing faces 35, 36. Because faces 35, 36 each have thin cross-sections, such faces only engage a minimum portion of a prepuce for blocking blood flow therethrough. Advantageously, more prepuce may be extended and severed above cavity 37 for ensuring that unnecessary prepuce portions do not remain attached to a penis after completing a circumcision procedure. In addition, because clamp 20 is preferably formed from plastic materials, a physician may monitor the location of the glans penis (not shown) with respect to engaging faces 35, 36 by simply looking through clamp 20 from above. Such an advantage will alleviate the necessity of lifting clamp 20 for monitoring the location of the glans penis and not severing same.

Arcuate portions 39, 40 have respective stepped sections 43, 44 interfaced and aligned with each other. Such sections cooperate with each other for opening and closing the engaging section about pivot connection 34. Hole 45 is provided through the center of sections 43, 44 for receiving pivot pin 30 therethrough. Such a pivot pin extends above top surface 38 of arcuate portion 40 and has a flattened top end 31 for securing same in place. Likewise bottom end 50 of pivot pin 30 is flattened.

Gap 46 exists between opposing arcuate portions 39, 40 when clamp 20 is at a closed position. Gap 46 is preferably about ¼" wide so that, when clamp 20 is moved to an open position, the distance between engaging faces 35, 36 at the same radial distance from the center of pivot connection 34 is also about ¼". Such a spatial relationship between faces 35, 36 prevents a glans penis from being engaged therebetween and thereby only allowing a prepuce to fit between such faces. Advantageously, the risk of engaging and damaging a glans penis during a circumcision procedure is substantially reduced.

After a prepuce is introduced between opposing faces 35, 36, it is important to tightly maintain such faces in a closed position. Doing so will assist to reduce blood flow in a prepuce section to be severed and thereby reduces the likelihood of excessive bleeding and infection after the procedure is completed. Also, the likelihood of having to stitch along the circumcision line is reduced because blood flowing thereto is substantially reduced.

Figure 3:
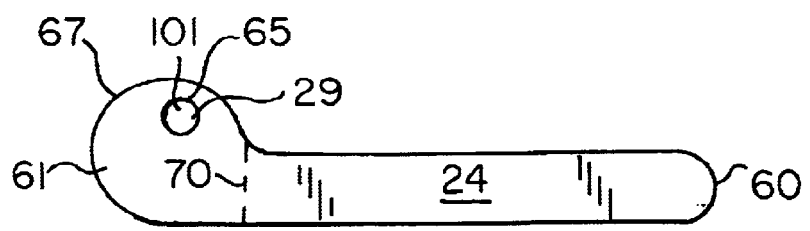
FIG. 3 is an enlarged top plan view of the handle shown in FIG. 1.
Figure 4:
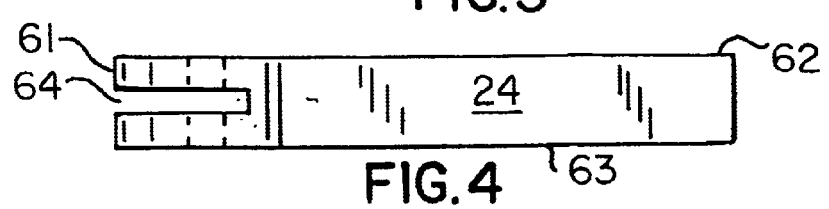
FIG. 4 is a front elevational view of the handle shown in FIG. 3.
Figure 5:
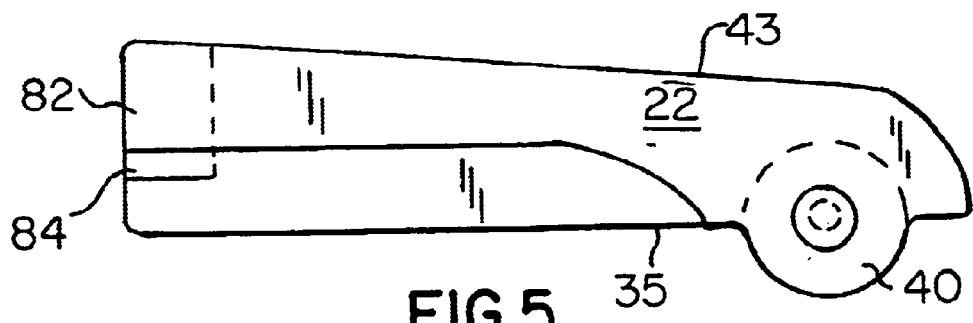
FIG. 5 is a reduced top plan view of the upper member shown in FIG. 1.
Figure 6:
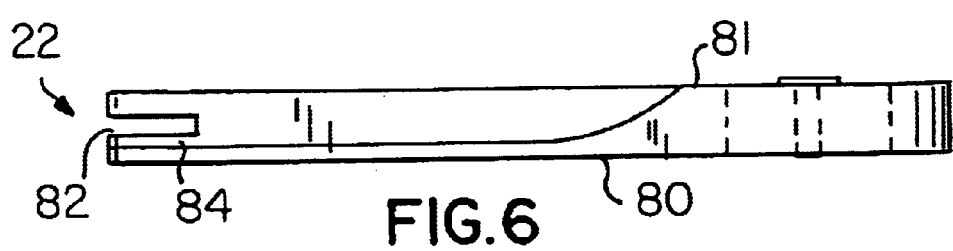
FIG. 6 is a front elevational view of the upper member shown in FIG. 5.
Figure 7:
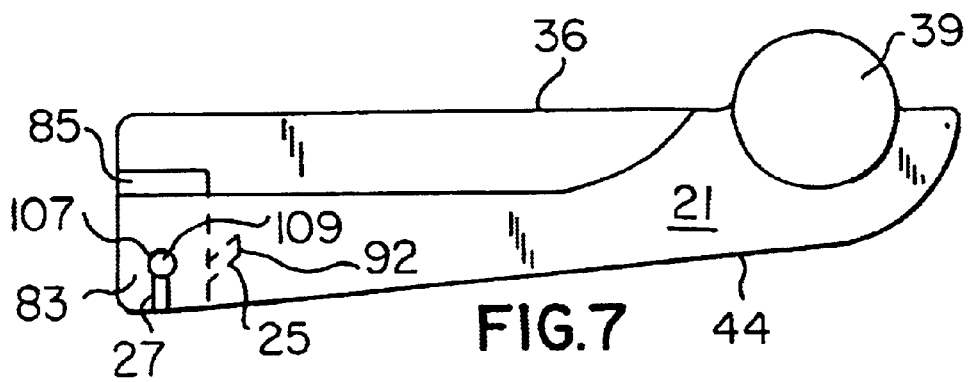
FIG. 7 is a reduced top plan view of the lower member shown in FIG. 1.
Figure 8:
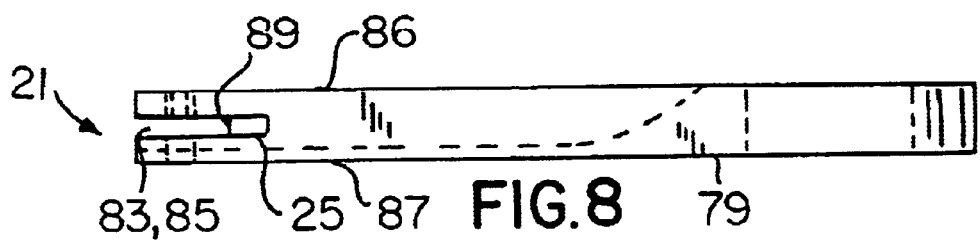
FIG. 8 is a front elevational view of the lower member shown in FIG. 7.
Figure 9:
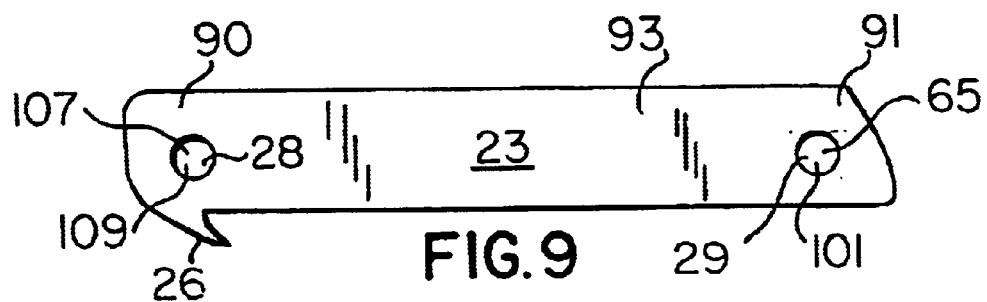
FIG. 9 is an enlarged top plan view of the latching member shown in FIG. 1.
Figure 10:
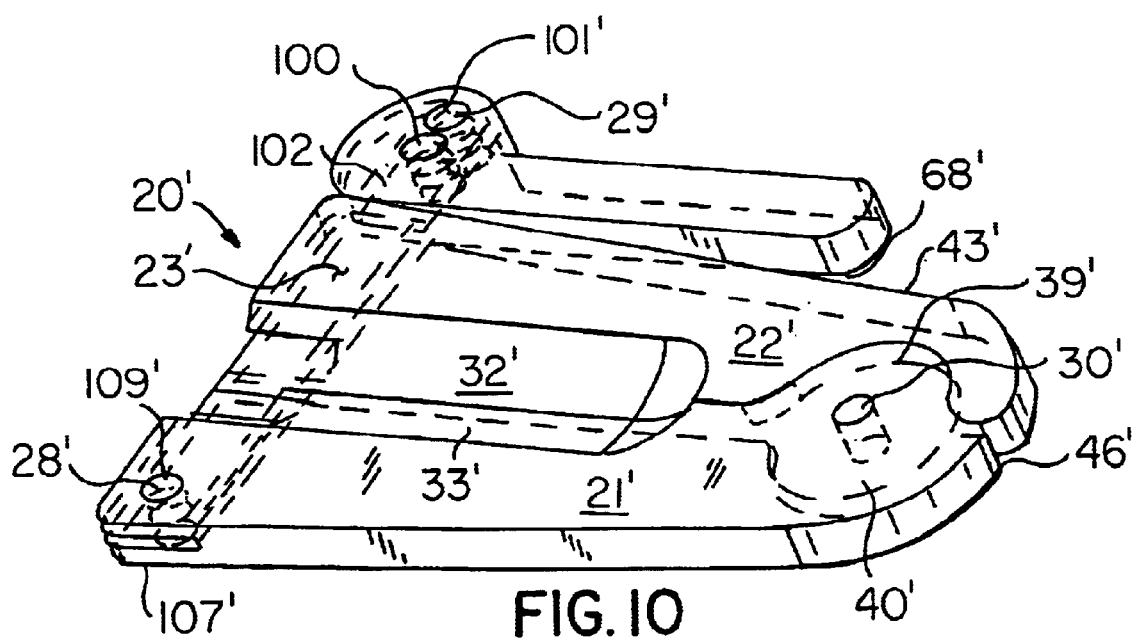
FIG. 10 is a perspective view showing a second embodiment of the circumcision clamp in accordance with the present invention.
Figure 11:
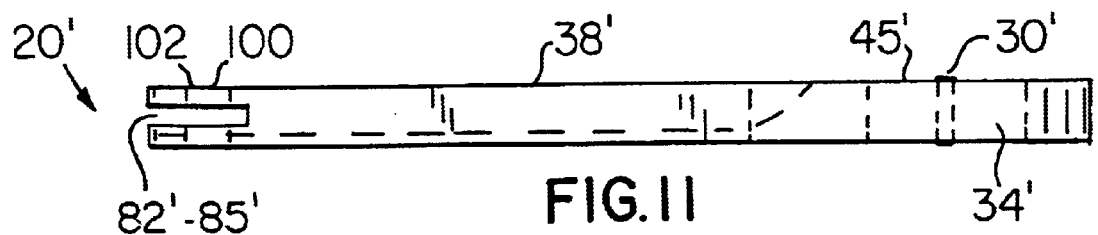
FIG. 11 is an enlarged front elevational view of the circumcision clamp shown in FIG. 10.
Figure 12:
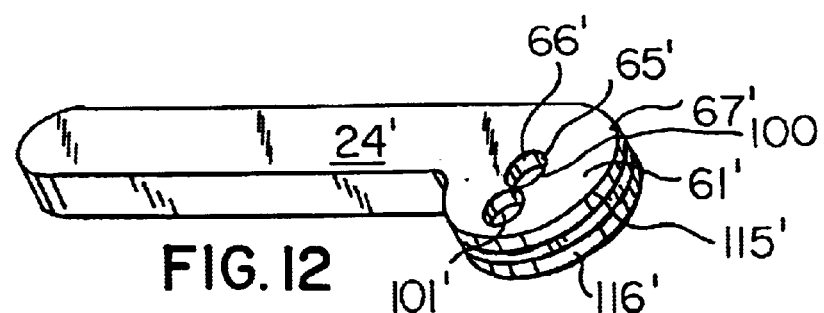
FIG. 12 is a perspective view of the handle shown in FIG. 10.
Figure 13:
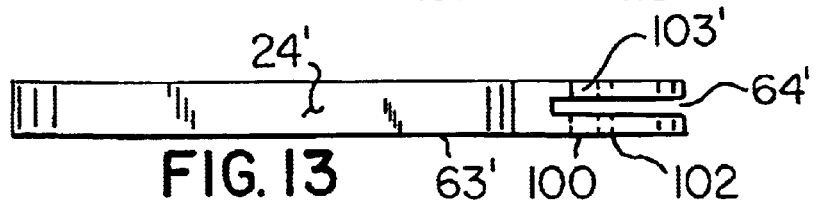
FIG. 13 is a front elevational view of the handle shown in FIG. 12.
Figure 14:
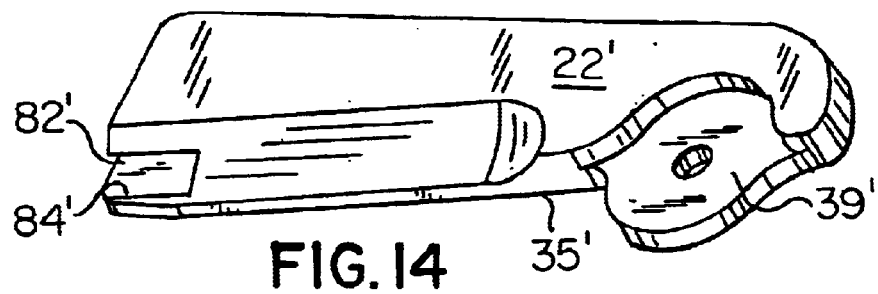
FIG. 14 is a reduced perspective view of the second member shown in FIG. 10.
Figure 15:
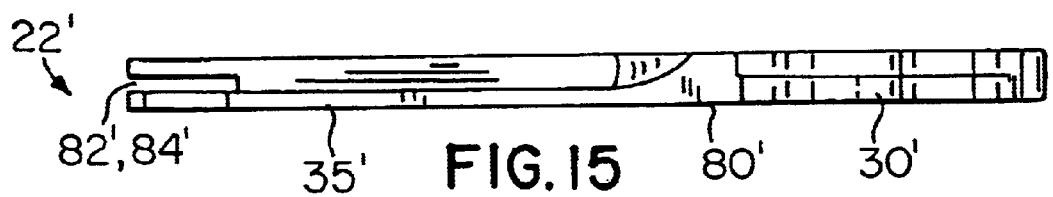
FIG. 15 is an enlarged front elevational view of the second member shown in FIG. 14.
Figure 16:
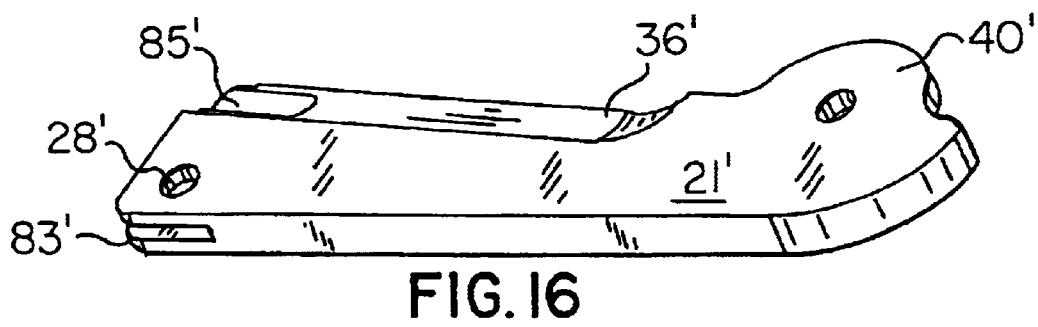
FIG. 16 is a reduced perspective view of the first member shown in FIG. 10.
Figure 17:
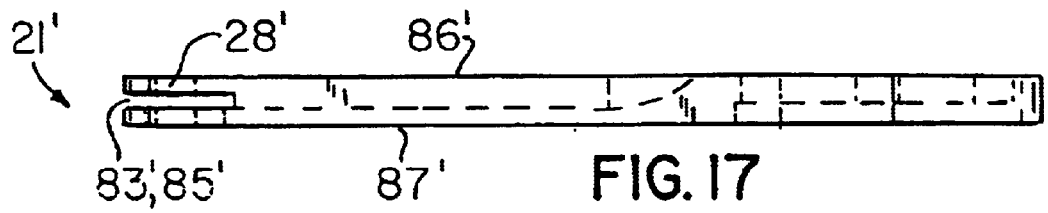
FIG. 17 is an enlarged front elevational view of the first member shown in FIG. 16.
Figure 18:
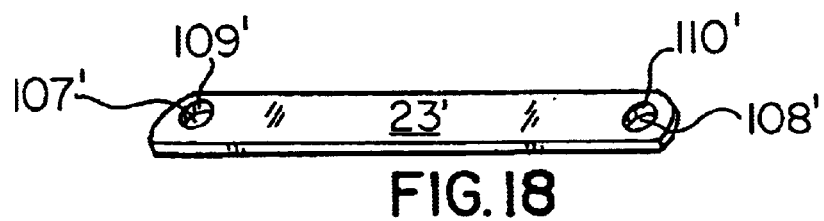
FIG. 18 is a reduced perspective view of the latching member shown in FIG. 10.
Figure 19:
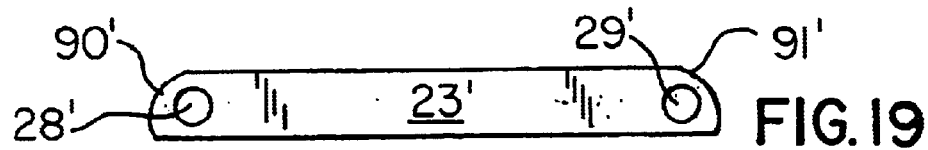
FIG. 19 is an enlarged top plan view of the latching member shown in FIG. 18.

Now referring to FIGS. 3 and 4, handle 24 has substantially arcuate ends 60, 61 with planar top and bottom surfaces 62, 63 extending along its length. Slot 64 is formed in arcuate end 61 generally midway between top and bottom surfaces 62, 63. Slot 64 is formed generally from perimeter 67 of arcuate end 61 and extends therefrom along the diameter of arcuate end 61 terminating at 70. Such a slot has a cross-section sufficient for allowing latching member 23 to be inserted therein and become pivotally connected to handle 24 via pivot connection 101.

Therefore, the width of handle 24 is greater than the width of latching member 23 and has substantially the same width as sides 43, 44 of first and second members. Hole 65 is spaced from the center of arcuate end 61 and closer to its perimeter 67 so that a communication is provided when closing the clamp. Pivot pin 29 is inserted into hole 65 and extends from top surface 62 of handle 24 through latching member 23 and down to bottom surface 63 of handle 24. Accordingly, pivot pin 29 secures latching member 23 and handle 24 together in a pivoting relationship.

Handle 24 extends adjacent to side 43 of second member 22 when clamp 20 is in a closed position. Further, handle 24 maintains a spatial relationship with side 43 when clamp 20 is in a closed position. Accordingly, arcuate portion 60 is spaced from side 43 and thereby forms gap 68. Such a gap extends from arcuate portion 60 and linearly decreases along the length of handle 24 until closely approaching arcuate portion 61. Arcuate end 61 forms the pivoting cam end of handle 24 and is of a larger diameter than arcuate end 60. Therefore, perimeter 67 of handle 24 maintains an engaged relationship with side 43 as handle 24 is pivoted about pivot connection 101 for initially opening and closing clamp 20. As handle 24 pivots about pivot connection 101, perimeter 67 of arcuate end 61 rolls along side 43 of second member 21.

For tightly maintaining clamp 20 in a closed position, a force must be exerted transverse to handle 24 and generally towards side 43 and in a clockwise direction until gap 68 wanes and arcuate portion 60 contacts side 43 of second member 22. This allows arcuate end 61 of handle 24 to serve as a cam and forcibly pull latching member 23 transversely across first and second members 21, 22. By doing so, first and second faces 35, 36 are firmly pressed against each other for tightly maintaining clamp 20 in a closed position.

Referring now to FIGS. 5–9, the shape of first member 21 is substantially symmetrical to the shape of second member 22. First and second members 21, 22 each have substantially planar bottom surfaces 79, 80. Each of such members has a slot 82, 83 for receiving a portion of latching member 23 as the securing means tightly maintains clamp 20 in a closed. Such slots extend from sides 43, 44 inwardly towards faces 35, 36 and have generally rectangular shapes with a cross-section sufficient for receiving latching member 23 therein. Slot portions 84, 85 respectively extend onto cavity portions 32, 33 but do not reach engaging faces 35, 36. Such slot portions allow latching member 23 to slide into and out of slots 82, 83 as latching member 23 pivots about pivot connection 107.

First member 21 further includes notch 25 formed generally midway between top and bottom surfaces 86, 87 of first member 21. Such a notch 25 extends from wall 89 of slot 83 in an upwardly sloped direction towards engaging face 36. Notch 25 is sufficiently deep for receiving spur 26 therein. Such a spur 26 protrudes from first end 90 of latching member 23 in such a direction so that spur 26 is aligned to fit into notch 25 when latching member 23 pivoted from its full open position 23" about pivot connection 107 into its full line position shown in FIG. 1. To assist in such an insertion, small smooth shoulder 92 provides a curved path for directing spur 26 into notch 25 so that the shoulder 92 spur 26 does not break off until the latching member 23 is thereafter pivoted to open the clamp after use.

In particular, shoulder 92 has an arc-like shape for spur 26 to slide thereagainst as latching member 23 is fully moved into slots 82, 83 for tightly maintaining clamp 20 in a closed position. For connecting latching member 23 to first member 21 and handle 24, latching member 23 has substantially planar top surface 93 and a bottom surface (not shown) and includes a pair of holes 109, 65 at respective ends 90, 91 passing through such surfaces. Such holes are aligned with corresponding hole 109 in first member 21 and hole 65 in handle 24 for receiving respective pivot pins 28, 29 therethrough.

First member 21 further includes passage or channel 27 adjacent or juxtaposed to pivot connection 107. The second end of the first member 21 is bifurcated and has upper portion 115 and lower portion 116. Such portions have passage 27. In alternate embodiments, at least one of upper and lower portions 115, 116 may have passage 27. Passage 27 extends generally downward from pivot connection 107 and provides a line of weakness for displacing pivot pin 28 and rendering clamp 20 inoperative after completing a circumcision procedure.

The width of passage 27 is narrower than the diameter of pivot pin 28 so that same will not prematurely become offset from its original position before a circumcision procedure is completed. Preferably, after first and second member 21, 22 move to an open position to receive prepuce between faces 35, 36, clamp 20 is then tightly maintained in a closed position by pressing handle 24 against sidewall 43. Spur 26 locks into notch 25 after latching member 23 has been pivoted about pivot connection 107 to position member 23 and into slots 82, 83 for closing clamp 20.

After a circumcision procedure is finished the handle 24 is pivoted about pivot connection 29 and latching member 23 is moved forwardly about pivot connection 107 from its stressed position to an open position and thereby disengages faces 35, 36. Such a pivoting movement about pivot connection 107 is resisted by spur 26 in notch 25. In particular, a resistive force opposes movement of latching member 23 to an open position. Such an opposing force applies a force to pivot pin 28 generally in the same direction of passage 27 or line of weakness. Accordingly, as latching member 23 is moving toward its broken line position 23" of FIG. 1, pin pivot 28 is forced outwardly at least partly into passage 27 and displaced from its original position. During this process, spur 26 may even fracture off shoulder 92.

The effect of displacing pivot pin 28 renders clamp 20 inoperative to be used again because the securing section can no longer tightly maintain the engaging section of the clamp in a tightly closed position. In particular, because pivot pin 28 is displaced from its original position, the pivoting axis at pivot connection 107 becomes loose, rather than firmly in place, and does not allow faces 35, 36 to be tightly maintained in a secure position.

It is noted that clamp 20 may be repeatedly opened and closed without displacing pivot pin 28 from its original position. However, latching member 23 should not be pivoted beyond the threshold point where spur 26 is moved past shoulder 92 and enters notch 25. If latching member 23 is pivoted beyond such a point, the risk of exerting pressure on pivot pin 28 and prematurely displacing pivot pin 28 from its original position likely may render the clamp inoperative for its intended purpose.

Now referring to FIGS. 10–16, a second embodiment 20' of clamp 20 is preferably made from aluminum. Aluminum may be processed with automated machinery, which is less expensive than conventional hand-milling procedures employed by some of the prior art. Advantageously, clamp 20' will be less expensive to manufacture than similar prior art clamps made from stainless steel, for example. Clamp 20' includes passage or channel 100 for permitting displacement of pivot pin 28' from its original position and for rendering clamp 20' useless until handle 24' and/or pivot pin 29' are replaced. Similar to clamp 20, clamp 20' includes first and second members 21', 22', latching member 23', and handle 24'. A main pivot connection 30' attaches first and second members 21', 22' to each other at one end and a pair of pivot connections 28', 29' attach first member 21' to latching member 23', and latching member 23' to handle 24', respectively.

Such an embodiment operates substantially the same as the previous embodiment for tightly maintaining faces 35', 36' in a closed position with prepuce engaged therebetween. However, in this embodiment pivot pin 29' is displaced from its original position rather than pivot pin 28 in the previous embodiment. In particular, after latching member 23' is positioned substantially in a vertical direction and inside slots 82', 83', handle 24' pivots about pivot connection 101' for moving clamp 20' to a closed position. Similar to handle 24, handle 24' also has gap 68' between itself and sidewall 43' of second member 22' when resting in a closed position. Accordingly, handle 24' should be pressed firmly against side 43' for tightly maintaining faces 35', 36' in a closed position. As a result, pressure is exerted against pivot pin 29' in the general direction of passage 100 thereby moving pivot pin 29' at least partially into passage 100.

Arcuate end 61' is bifurcated and has upper and lower portions 115', 116'. Such portions have passage 100. In alternate embodiments, at least one of upper and lower portions 115', 116' may have passage 100. Passage 100 is adjacent pivot connection 101' and extends in a generally parallel direction to the length of latching member 23' when clamp 20' is in a closed position. In alternate embodiments, passage 100 may be juxtaposed to pivot connection 101'.

Accordingly, as handle 24' is pivoted in a counter clockwise motion from a closed position to an open position after the circumcision, a force is exerted on pivot pin 29' and in the general direction of passage 100 so that pivot pin 29' will be displaced along passage 100 and away from its original position. After pivot pin 29' has been displaced from its original position, clamp 20' becomes useless due to the inoperability of pivot connection 101'. Pivot connection 101' becomes inoperable thereby not providing a secure pivoting point for the cam of handle 24' to exert a sufficient closing force on the clamp 20'. Similar to passage 27 in clamp 20, passage 100 may have a width that is narrower than the diameter of pivot pin 29' for preventing same from prematurely being displaced from its original position before a circumcision operation is performed.

Advantageously, although clamp 20' is not operable after pivot pin 29' is displaced from its original position, such a clamp may be refurbished and sterilized for further use. In particular, clamp 20' may be reused after handle 24' is replaced with a new handle (not shown). The pivot connection 101' may also be replaced by a new pivot pin (not shown). To replace handle 24', clamp 20' preferably should be returned to the manufacturer. The manufacturer may than properly replace handle 24' and sterilized clamp 20' for resale and/or reuse. Replacing handle 24' is a fairly simple task but should be performed by the manufacturer for ensuring proper functioning and sterilization, prior to each reuse of clamp 20'. Such a feature of clamp 20' assists in the reduction patients' costs and prevents unnecessary disposal of the entire clamp 20'.

While the invention has been described with respect to certain specific embodiments, it will be appreciated that many modifications and changes may be made by those skilled in the art without departing from the spirit of the invention. It is intended, therefore, by the appended claims to cover all such modifications and changes as fall within the true spirit and scope of the invention.

What is claimed as new and what it is desired to secure by Letters Patent of the United States is:

1. A circumcision clamp for performing a circumcision operation, said clamp comprising:
    an engaging section for receiving prepuce to be removed during a circumcision procedure;
    securing means for tightly maintaining said engaging section in a closed position and for releasing said engaging section to be opened, said securing means including a latching member and a handle movably connected thereto;
    a pair of pivot connections for respectively connecting a first end of said latching member to said engaging section and a second end of said latching member to said handle, each of said pivot connections including a pivot pin; and
    a passage adjacent one of said pivot connections into which a corresponding one said pivot pin is at least partially displaceable when force is exerted against said one pivot pin in a direction generally toward said passage for causing said one pivot pin to be displaced from its original position into a position in which said circumcision clamp becomes inoperative.

2. The circumcision clamp of claim 1, wherein said engaging section includes an elongate first member and an elongate second member and a main pivot connection adjacent a first end of each member for movably connecting said first and second members, said first and second members being formed of transparent plastic material for allowing a circumcision operator to monitor glans penis therebeneath so that same is not damaged during a circumcision.

3. The circumcision clamp of claim 2, wherein said first end of said latching member includes a spur for resisting movement of said securing means from a closed position to an open position, said first member having a notch generally at a second end thereof and adjacent said spur so that when said securing means is moved to a closed position said spur slips into said notch, said spur and notch resisting movement of said securing means and causing said one pivot pin to be forcibly displaced from its original position into said inoperative position.

4. The circumcision clamp of claim 3, wherein said notch has a generally smooth shoulder for guiding said spur therein when said latching member is moved to a closed position.

5. The circumcision clamp of claim 3, wherein said notch is generally midway between upper and lower surfaces of said second end of said first member.

6. The circumcision clamp of claim 2, wherein said passage is located at said second end of said first member, said passage extending from said one pivot connection towards an outer edge of said first member.

7. The circumcision clamp of claim 2, wherein said latching member and pins are formed of steel and remaining elements of said clamp are formed of plastic material.

8. The circumcision clamp of claim 2, wherein said passage is juxtaposed to said one pivot connection in said first member.

9. The circumcision clamp of claim 2, wherein said second end of said first member is bifurcated and has an upper portion and a lower portion for receiving said first end of said latching member therebetween, said passage being located in at least one said bifurcated upper and lower portion of said first member.

10. The circumcision clamp of claim 1, wherein said one pivot connection is formed of deformable material so that said one pivot pin at least partially enters said passage when said latching member is moved to an open position after a circumcision.

11. The circumcision clamp of claim 1, wherein said passage has a width narrower than the diameter of said one pivot pin so that same can only partially enter said passage when sufficient pressure is applied to said one pivot pin in a general direction of said passage.

12. A circumcision clamp for performing a circumcision operation, said clamp comprising:
    an engaging section for receiving prepuce to be removed during a circumcision procedure;
    securing means for tightly maintaining said engaging section in a closed position and for releasing said engaging section to be opened, said securing means including a latching member and an elongated handle movably connected thereto;
    a pair of pivot connections for respectively connecting a first end of said latching member to said engaging section and a second end of said latching member to one end of said handle, each of said pivot connections including a pivot pin; and
    said one end of said handle having a passage into which one said pivot pins is at least partially displaceable when force is exerted against said one pivot pin in a direction generally toward said passage to cause said one pivot pin to be displaced from its original position into a position in which said circumcision clamp becomes inoperative.

13. The circumcision clamp of claim 12, wherein said one end of said handle is bifurcated and has an upper portion and a lower portion for receiving said latching member therebetween, said passage being located in at least one said upper and lower portion of said bifurcated end.

14. The circumcision clamp of claim 12, wherein said passage is adjacent one said pivot connection.

15. The circumcision clamp of claim 12, wherein said engaging section includes an elongate first member and an elongate second member and a main pivot connection adjacent a first end of each member for movably connecting said first and second members.

16. The circumcision clamp of claim 12, wherein said passage at least partially receives said one pivot pin from said original position when said securing means is moved to an open position after a circumcision.

17. The circumcision clamp of claim 12, wherein said one pivot connection is formed of deformable material so that said one pivot pin at least partially enters said passage when said securing means is moved to an open position after a circumcision.

18. The circumcision clamp of claim 12, wherein said passage has a width narrower than the diameter of said one pivot pin so that said one pivot pin can only partially enter said passage when sufficient pressure is applied to said one pivot pin in a general direction of said passage.

19. The circumcision clamp of claim 18, wherein said latching member and pins are formed of steel and remaining elements of said clamp are formed of aluminum.

* * * * *